(12) United States Patent
Abe et al.

(10) Patent No.: US 10,082,480 B2
(45) Date of Patent: Sep. 25, 2018

(54) GAS CONCENTRATION DETECTION DEVICE

(71) Applicant: NGK SPARK PLUG CO., LTD., Nagoya-shi, Aichi (JP)

(72) Inventors: Satoru Abe, Ichinomiya (JP); Tomonori Uemura, Komaki (JP); Tetsuya Ito, North Nagoya (JP); Satoshi Teramoto, Nisshin (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 0 days.

(21) Appl. No.: 15/597,826

(22) Filed: May 17, 2017

(65) Prior Publication Data
US 2017/0336342 A1 Nov. 23, 2017

(30) Foreign Application Priority Data
May 19, 2016 (JP) .................. 2016-100623

(51) Int. Cl.
  *G01N 27/409* (2006.01)
  *G01N 27/407* (2006.01)
  *G01N 33/00* (2006.01)

(52) U.S. Cl.
  CPC ....... *G01N 27/409* (2013.01); *G01N 27/4073* (2013.01); *G01N 33/0036* (2013.01)

(58) Field of Classification Search
  CPC ...... G01N 27/00; G01N 27/26; G01N 27/403; G01N 27/406; G01N 27/407; G01N 27/4073; G01N 27/409; G01N 27/413; G01N 27/4162; G01N 27/417; G01N 27/419; G01N 27/42; G01N 33/0036
  USPC ....... 324/425, 439, 444, 446, 600, 649, 691, 324/713, 76.11; 204/193, 194, 400, 421, 204/424, 426; 702/1, 57, 64
  See application file for complete search history.

(56) References Cited

U.S. PATENT DOCUMENTS

| | | | | |
|---|---|---|---|---|
| 7,445,698 B2 * | 11/2008 | Hada | ............... | G01N 27/4071 204/401 |
| 7,938,944 B2 * | 5/2011 | Suzuki | ............... | G01N 33/0037 204/426 |
| 8,182,664 B2 * | 5/2012 | Hiraiwa | ............... | G01N 27/4067 204/424 |
| 9,518,954 B2 * | 12/2016 | Ishiguro | ............... | G01N 27/4175 |
| 2004/0195097 A1 | 10/2004 | Suzuki et al. | | |
| 2007/0215470 A1 * | 9/2007 | Kawase | ............... | G01N 27/4065 204/424 |
| 2017/0336344 A1 * | 11/2017 | Uemura | ............... | G01N 27/41 |

FOREIGN PATENT DOCUMENTS

JP 4124119 B2 7/2008

* cited by examiner

*Primary Examiner* — Hoai-An D Nguyen
(74) *Attorney, Agent, or Firm* — Sughrue Mion, PLLC

(57) ABSTRACT

A gas concentration detection device for detecting a gas concentration using a limiting current type gas concentration sensor. In an application voltage line set to pass through a plurality of limiting current regions for different values of gas concentration, a ratio for lean is set as a ratio of change in current with respect to a change in voltage when an air/fuel ratio corresponding to the gas concentration is lean, and a ratio of rich different from the ratio for lean is set when the air/fuel ratio is rich.

5 Claims, 8 Drawing Sheets

GAS CONCENTRATION DETECTION DEVICE

BACKGROUND OF THE INVENTION

1. Field of the Invention

The present invention relates to a gas concentration detection device for detecting the concentration of a specific gas contained in a gas to be measured.

2. Description of the Related Art

Conventionally, for example, a limiting current type air/fuel ratio sensor is known as a device for detecting the concentration (i.e., air/fuel ratio: A/F) of oxygen in an exhaust gas discharged from an engine of a vehicle.

This type of air/fuel ratio sensor has, as a sensor element, for example, a solid electrolyte and a pair of electrodes formed thereon, and is configured such that current (pump current Ip) corresponding to oxygen concentration flows by applying a voltage (application voltage Vp) between the pair of electrodes.

FIG. 4A shows output characteristics indicating the relationship between pump current Ip and application voltage Vp of the above sensor element. In the output characteristics, a flat region parallel to the voltage axis, i.e., a region (limiting current region) GD of limiting current is known in which the pump current Ip is constant. In addition, the pump current Ip in the limiting current region GD is known to increase as the oxygen concentration increases.

Therefore, conventionally, an application voltage Vp corresponding to the limiting current region GD is applied to the sensor element, and the oxygen concentration is detected from the resulting pump current Ip. That is, the oxygen concentration (i.e., air/fuel ratio) is detected by a so-called limiting current method.

In the above technique, in order to detect the air/fuel ratio accurately, it is necessary to control the application voltage Vp in a range corresponding to the limiting current region GD. Therefore, normally, using a linear function indicating a straight line, an application voltage line ID indicating the relationship between the application voltage Vp and the pump current Ip (for determining the application voltage Vp) is set, and then the application voltage Vp is determined using the application voltage line ID.

However, as shown in FIG. 4B, the output characteristics and the limiting current region GD change depending on the temperature (high-temperature side H, low-temperature side L). Therefore, in recent years, a new method for setting the application voltage line ID has been proposed (see, for example, Patent Document 1).

In this measurement method, the application voltage line ID is set using a single straight line (linear function) so as to pass through a region in which the limiting current regions GD of a plurality of output characteristics (high-temperature side H, low-temperature side L) for different temperature conditions overlap each other.

[Patent Document 1] Japanese Patent No. 4124119

PROBLEMS TO BE SOLVED BY THE INVENTION

However, the conventional technique in which the application voltage line ID is set using a single straight line merely by considering a temperature condition as described above is not always sufficient.

That is, in practice, depending on the gas atmosphere (i.e., oxygen concentration) or variation among individual sensor elements, the resistance value of the solid electrolyte thereof varies, and therefore there is a possibility that the detection accuracy of the oxygen concentration is deteriorated.

For example, even if the temperature condition is considered, depending on the oxygen concentration (for example, in a rich case where the amount of fuel is larger than in a stoichiometric state), the application voltage line ID using a single straight line can deviate from the limiting current regions GD. In such a case, even if control using the application voltage line ID is performed, the oxygen concentration cannot be accurately detected.

SUMMARY OF THE INVENTION

It is therefore an object of the present invention to provide a gas concentration detection device capable of accurately detecting a gas concentration in the case of detecting gas concentration using a limiting current type gas concentration sensor.

The above object of the invention has been achieved by providing:

(1) In a first aspect, the present invention relates to a gas concentration detection device, adapted for a gas concentration sensor including a sensor element having: a solid electrolyte having oxygen ion conductivity; and a pair of electrodes formed on the solid electrolyte, the gas concentration detection device being configured to apply a voltage between the pair of electrodes based on an application voltage line which is a linear function having an intercept at a predetermined voltage value, detect limiting current flowing between the pair of electrodes in accordance with the voltage, and detect a gas concentration of a specific component in a gas to be measured, based on the limiting current.

In the gas concentration detection device (1), in a detection range for detecting the gas concentration, the application voltage line is set so as to pass through a plurality of limiting current regions of: respective limiting current regions for different values of the gas concentration; and a region in which respective limiting current regions for different temperature conditions of the sensor element overlap each other. In addition, a ratio of change in current with respect to a change in voltage in the application voltage line is set as a ratio for lean when an air/fuel ratio corresponding to the gas concentration is lean, and a ratio for rich different from the ratio for lean is set when the air/fuel ratio is rich.

Thus, in the first aspect, as a basic configuration, the application voltage line is set so as to pass through respective limiting current regions for different gas concentrations and to pass through a region in which respective limiting current regions for different temperature conditions of the sensor element overlap each other.

In addition, in the first aspect, in the basic configuration described above, the ratio of change in current with respect to a change in voltage in the application voltage line (which is a linear function) is set as a ratio for lean when the air/fuel ratio corresponding to the gas concentration is lean, and the ratio for rich which is different from the ratio for lean is set when the air/fuel ratio is rich. As a result, it is possible to accurately detect the gas concentration (specifically, air/fuel ratio).

That is, even when considering the temperature condition, for example, depending on the oxygen concentration or the like, the application voltage line using a single straight line can deviate from some limiting current regions. In this case, it might be nearly impossible to accurately detect, for example, the oxygen concentration, even if control using this application voltage line is performed.

However, in the first aspect, a ratio (i.e., a ratio of change in current with respect to a change in voltage) that differs between a lean case and a rich case is set, so as to prevent the application voltage line from deviating from the limiting current regions. Therefore, by using the application voltage line set as described above, it is possible to detect the gas concentration (specifically, air/fuel ratio) with higher accuracy.

(2) In a second aspect which is a preferred embodiment of the gas concentration detection device (1), the ratio for lean is greater than the ratio for rich.

The second aspect exemplifies a preferred method for setting the ratio of change in current with respect to a change in voltage. By thus setting the ratio for lean and the ratio for rich, it is possible to set a preferable application voltage line (i.e., an application voltage line that is unlikely to deviate from the limiting current regions) that matches actual voltage current characteristics.

(3) In a third aspect which is a preferred embodiment of the gas concentration detection device (1) or (2) above, the gas concentration device is configured to switch between the ratio for rich and the ratio for lean based on the limiting current flowing between the pair of electrodes.

The third aspect exemplifies a preferable setting method for the ratio of change in current with respect to a change in voltage. Since the limiting current flowing between the pair of electrodes corresponds to the gas concentration (specifically, air/fuel ratio), switching between the ratio for lean and the ratio for rich is carried out in accordance with the limiting current, whereby the application voltage line is set so as to be unlikely to deviate from the limiting current regions. That is, the slope of the application voltage line is set depending on the detecting limiting current value (4) In the fourth aspect which is a preferred embodiment of the gas concentration detection device of any of (1) to (3) above, when the air/fuel ratio is lean and the ratio for lean is set, the gas concentration detection device is configured so that the ratio for lean remains set within a rich-side hysteresis range set in a predetermined rich-side range from a stoichiometric state when the air/fuel ratio changes from lean to rich.

In the fourth aspect, hysteresis (e.g., a lag time) is set to time the switching between the ratio for lean and the ratio for rich. When the air/fuel ratio changes from lean to rich, the ratio for lean remains set within the rich-side hysteresis range. Then, when the air/fuel ratio exceeds (on the rich side) the rich-side hysteresis range, the ratio is switched to rich.

For example, when the air/fuel ratio becomes stoichiometric, instead of immediately switching between the ratio for lean and the ratio for rich, a timing of the switching is shifted, whereby switching between the ratio for lean and the ratio for rich can be prevented from occurring frequently in or near a stoichiometric state.

In particular, in the case where the target air/fuel ratio is set at a stoichiometric ratio, by setting hysteresis as described above, frequent switching between the ratio for lean and the ratio for rich can be prevented, and therefore there is an advantage that the air/fuel ratio can be stably controlled at the target air/fuel ratio.

(5) In the fifth aspect which is a preferred embodiment of the gas concentration detection device of any of (1) to (3) above, when the air/fuel ratio is rich and the ratio for rich is set, the gas concentration detection device is configured so that the ratio for rich remains set within a lean-side hysteresis range set in a predetermined lean-side range from a stoichiometric state when the air/fuel ratio is changed from rich to lean.

In the fifth aspect, as in the fourth aspect, hysteresis is set to time the switching between the ratio for lean and the ratio for rich. When the air/fuel ratio changes from rich to lean, the ratio for rich remains set within the lean-side hysteresis range. Then, when the air/fuel ratio exceeds (on the lean side) the lean-side hysteresis range, the ratio is switched to lean.

The fifth aspect provides the same effect as the fourth aspect.

Hereinafter, various configurations of the present invention will be described.

The limiting current is, as is well known, a current value in a region (limiting current region) in which, even if the voltage applied between the pair of electrodes changes, the value of current flowing between the pair of electrodes does not substantially change. The limiting current corresponds to a gas concentration (e.g., oxygen concentration or air/fuel ratio).

The air/fuel ratio is the mass ratio (A/F) of air (A) with respect to fuel (F). Here, a lean air/fuel ratio indicates that the amount of fuel is smaller than in a stoichiometric air/fuel ratio (stoichiometric state), and a rich air/fuel ratio indicates that the amount of fuel is larger than in a stoichiometric state.

The application voltage line has an intercept at a predetermined voltage value and defines, by a linear function, the relationship between voltage applied between the pair of electrodes and current flowing through the pair of electrodes. The application voltage line is set so as to pass through a plurality of limiting current regions for a plurality of gas concentrations (specifically, air/fuel ratios).

Therefore, using the application voltage line, by, for example, setting current, the voltage applied between the pair of electrodes can be calculated.

A formula (A) defining the application voltage line in a voltage-current coordinate system (as an in x-y coordinate system) is as follows.

$$\text{Voltage } Vp = \text{current } Ip \times \alpha + \text{fixed value } a \quad (A)$$

Here, as $\alpha$, an internal resistance $Ri$ for DC (direct current) passing through the sensor element (specifically, solid electrolyte) can be used. It is noted that the fixed value a is an intercept on the voltage value (at current $Ip=0$).

The formula (A) can be rearranged as the following formula (B).

$$\text{Current } Ip = \text{voltage } Vp \times \beta + \text{fixed value } b \quad (B)$$

Here, $\beta$ is the reciprocal of a and can be represented as $(1/Ri)$. The fixed value b is an intercept on the current value (at voltage $Vp=0$).

The "ratio $(\Delta Ip/\Delta Vp)$ of change $(\Delta Ip)$ in current with respect to a change $(\Delta Vp)$ in voltage" corresponds to $\beta$ in formula (B), for example. That is, for example, in the case of representing the application voltage line ID in a voltage-current coordinate system as shown in FIG. 4A, $\beta$ is the slope of the application voltage line ID.

Rich-side hysteresis is a history effect (history phenomenon) that keeps the ratio for lean during a predetermined period when the air/fuel ratio changes from the lean side to the rich side. Lean-side hysteresis is a history effect (history phenomenon) that keeps the ratio for rich during a predetermined period when the air/fuel ratio changes from the rich side to the lean side.

Such hysteresis can be set based on the limiting current flowing between the pair of electrodes, for example. In addition, for example, the hysteresis can be set based on a counter that changes in response to the elapsed time from a stoichiometric state.

EFFECTS OF THE INVENTION

The gas concentration detection device of the present invention enhances the detection accuracy in detecting the concentration of a specific gas in a gas to be measured.

DESCRIPTION OF REFERENCE NUMERALS

Figure 1:
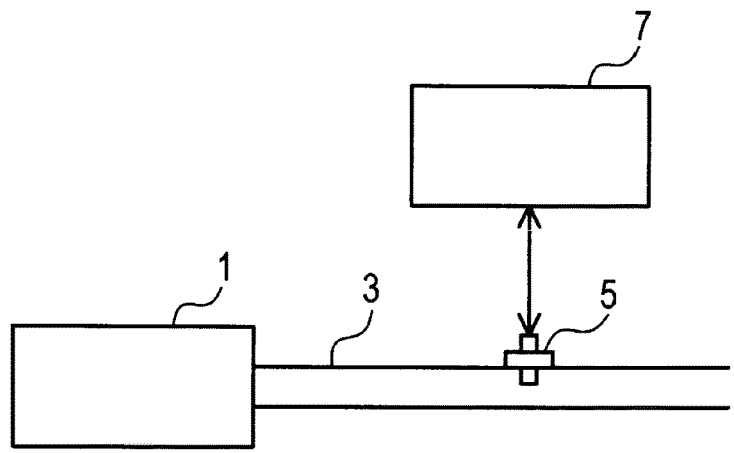
FIG. 1 is an explanatory view which illustrates the system configuration of an air/fuel ratio sensor and a gas concentration detection device in a first embodiment.

Reference numerals used to identify various features in the drawings include the following.

5: air/fuel ratio sensor; 9: sensor element; 7: gas concentration detection device; 11: solid electrolyte layer; 21: measurement chamber; 23: reference oxygen chamber; 25: first electrode; 27: second electrode

DETAILED DESCRIPTION OF THE PREFERRED EMBODIMENTS

Hereinafter, the present invention will be described in detail with reference to the drawings. However, the present invention should not be construed as being limited thereto.

In the following embodiments, a gas concentration detection device that measures gas concentration using an air/fuel ratio sensor which is a type of gas concentration sensor is described as an example.

1. First Embodiment

1-1. Entire Configuration

First, the entire configuration of a system relevant to a gas concentration detection device in the first embodiment will be described.

As shown in FIG. 1, in the first embodiment, for example, an air/fuel ratio sensor 5 is attached to an exhaust pipe 3 of an engine 1 of a vehicle, and a gas concentration detection device 7 detects an oxygen concentration (i.e., air/fuel ratio) in an exhaust gas discharged from the engine 1, based on the output from the air/fuel ratio sensor 5.

Figure 2:
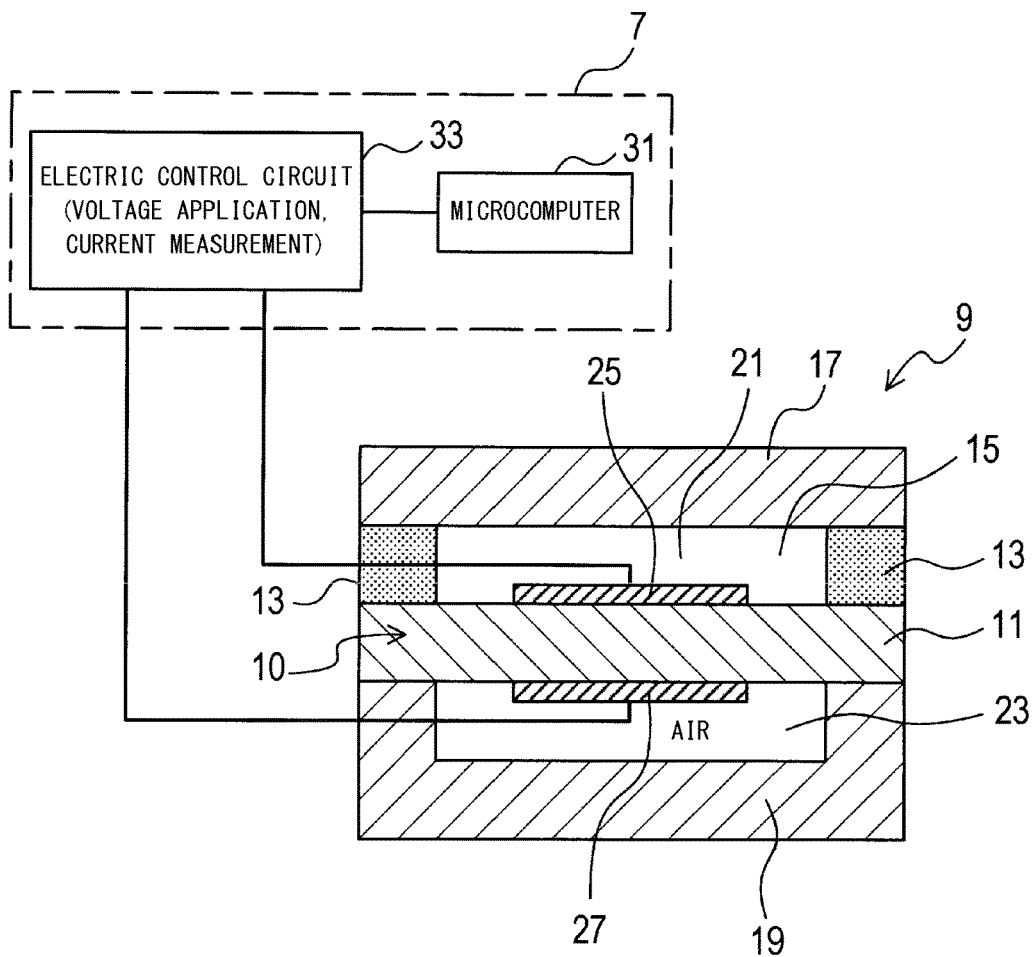
FIG. 2 is an explanatory cutaway view of a sensor element in the first embodiment along the thickness direction (i.e., A-A cross-section in FIG. 3), as well as its electrical configuration.
Figure 3:
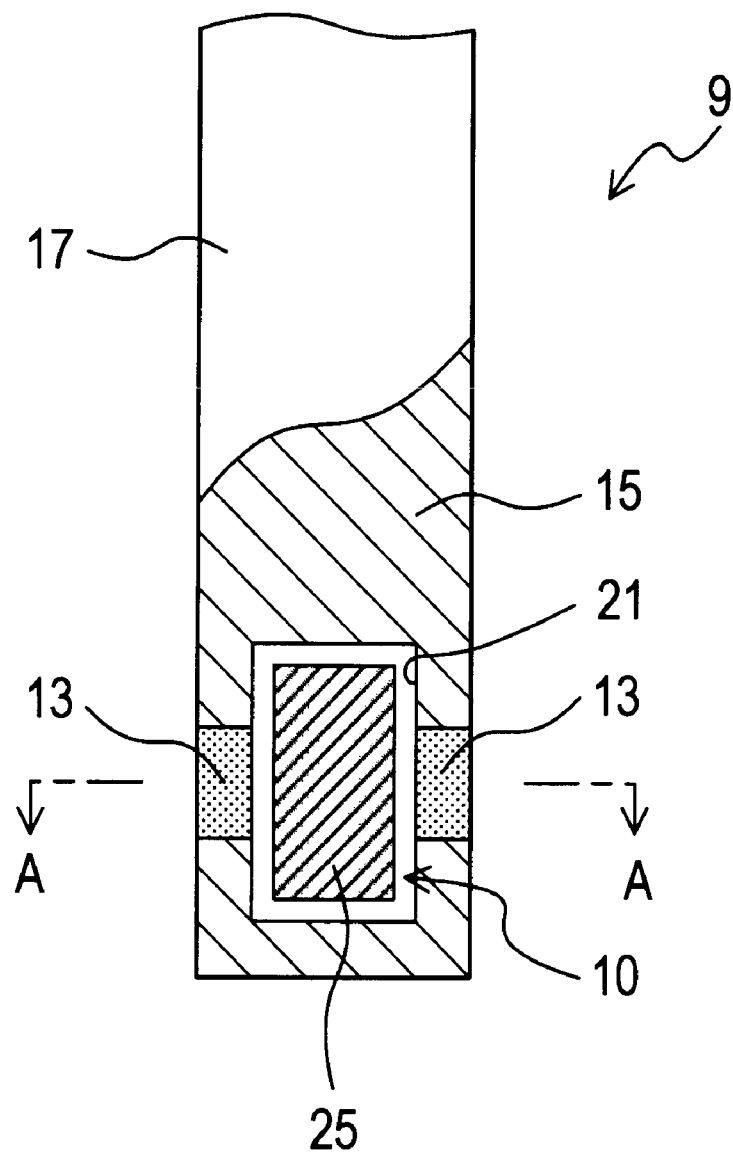
FIG. 3 is an explanatory partially-cutaway view of the sensor element in the first embodiment, as viewed from the thickness direction.

As shown in FIG. 2 and FIG. 3, the air/fuel ratio sensor 5 includes a stacked type sensor element 9 for detecting the oxygen concentration. The sensor element 9 is an elongated element and housed in a housing or the like (not shown).

More specifically, the sensor element 9 includes, in a layer form, a solid electrolyte (solid electrolyte layer) 11, a diffusion resistance layer 13, an intermediate insulating layer 15, a first outside insulating layer 17, and a second outside insulating layer 19, and includes a measurement chamber 21 and a reference oxygen chamber 23.

Among these, the solid electrolyte layer 11 is a rectangular plate material made from, for example, partially stabilized zirconia, and has a surface that faces the measurement chamber 21 and on which a first electrode 25 is formed, and a surface that faces the reference oxygen chamber 23 and on which a second electrode 27 is formed. That is, a pair of the first electrode 25 and the second electrode 27 are arranged so as to oppose each other with the solid electrolyte layer 11 therebetween. The electrodes 25, 27 are made from, for example, platinum. Here, the solid electrolyte layer 11 provided with the electrodes 25, 27 is referred to as an element portion 10.

The diffusion resistance layer 13 is a porous layer provided between the solid electrolyte layer 11 and the first outside insulating layer 17, and is made from alumina, zirconia, or the like, for example. An exhaust gas is introduced from outside (space in exhaust pipe 3) into the measurement chamber 21 through the diffusion resistance layer 13 so as to control diffusion of the exhaust gas.

The intermediate insulating layer 15 is a dense layer (layer formed so as not to allow gas penetration) provided between the solid electrolyte layer 11 and the first outside insulating layer 17, and is made from alumina, zirconia, or the like, for example. The intermediate insulating layer 15 together with the diffusion resistance layer 13 is provided so as to surround the periphery of the measurement chamber 21.

The first outside insulating layer 17 is a dense layer covering the measurement chamber 21, the intermediate insulating layer 15, and the diffusion resistance layer 13 from above in FIG. 2, and is made from alumina, zirconia, or the like, for example.

The second outside insulating layer 19 is a dense layer covering the periphery of the reference oxygen chamber 23, and is made from alumina, zirconia, or the like, for example. Although not shown, a heater for heating the sensor element 9 is embedded in the second outside insulating layer 19.

The measurement chamber 21 is a rectangular parallelepiped space into which an exhaust gas is introduced via the diffusion resistance layer 13 from the outside, and the first electrode 25 is formed on the solid electrolyte layer 11 inside the measurement chamber 21.

The reference oxygen chamber 23 is an elongated space into which air is introduced, and opens upward in FIG. 3.

The second electrode 27 is formed on the solid electrolyte layer 11 inside the reference oxygen chamber 23.

Next, the electric configuration of the gas concentration detection device 7 will be described.

As shown in FIG. 2, the gas concentration detection device 7 is a device for controlling the operation of the sensor element 9 (i.e., the air/fuel ratio sensor 5) and detecting the oxygen concentration (i.e., the air/fuel ratio) in the exhaust gas, and includes an electric control circuit 33 and a microcomputer 31 programmed to direct the operation of the electronic control circuit 33.

The microcomputer 31 is an electronic control device including known CPU, ROM, RAM, and the like. The ROM stores data, such as an application voltage line and hysteresis, needed for control.

The electric control circuit 33 is a known circuit capable of applying a voltage (application voltage Vp) between the electrodes 25, 27 and measuring current (pump current Ip) flowing between the electrodes 25, 27, and is controlled by the microcomputer 31.

1-2. Basic Operation

Next, pumping of oxygen, which is a basic operation of the air/fuel ratio sensor 5, will be described.

As shown in FIG. 2, in the sensor element 9, an ambient exhaust gas is introduced into the measurement chamber 21 via the diffusion resistance layer 13. Here, the case where a positive voltage is applied to the first electrode 25 and a negative voltage is applied to the second electrode 25 will be described.

First, in the case where the amount of fuel in the exhaust gas is such that the air/fuel ratio is greater than a stoichiometric state (stoichiometric air/fuel ratio: A/F=14.7) (a so-called lean case), oxygen in the exhaust gas is decomposed into oxygen ions at the first electrode 25 by applying a voltage (application voltage Vp) between the electrodes 25, 27.

The oxygen ions then pass through the solid electrolyte layer 11 from the first electrode 25, to be supplied to the second electrode 27, and then are discharged as oxygen from the second electrode 27 to the reference oxygen chamber 23. As a result, oxygen is pumped out of the measurement chamber 21. Thus, a current (pump current Ip) which is positive current flows from the second electrode 27 side to the first electrode 25 side.

On the other hand, in the case where the amount of fuel in the exhaust gas is such that the air/fuel ratio is less than a stoichiometric state (a so-called rich case), opposite the lean case, oxygen in the reference oxygen chamber 23 is decomposed into oxygen ions at the second electrode 27.

Then, the decomposed oxygen ions pass through the solid electrolyte layer 11 from the second electrode 27, to be supplied to the first electrode 25, and then are discharged as oxygen from the first electrode 25 to the measurement chamber 21. As a result, oxygen is pumped into the measurement chamber 21. Thus, a current which is a negative current flows from the first electrode 25 side to the second electrode 27 side.

Therefore, as described in detail below, the air/fuel ratio of the exhaust gas can be detected based on the pump current Ip described above.

1-3. Relationship Between Voltage and Current

Next, the relationship between the application voltage Vp and the pump current Ip, and the application voltage line ID used in gas concentration detection will be described.

Figure 4A:
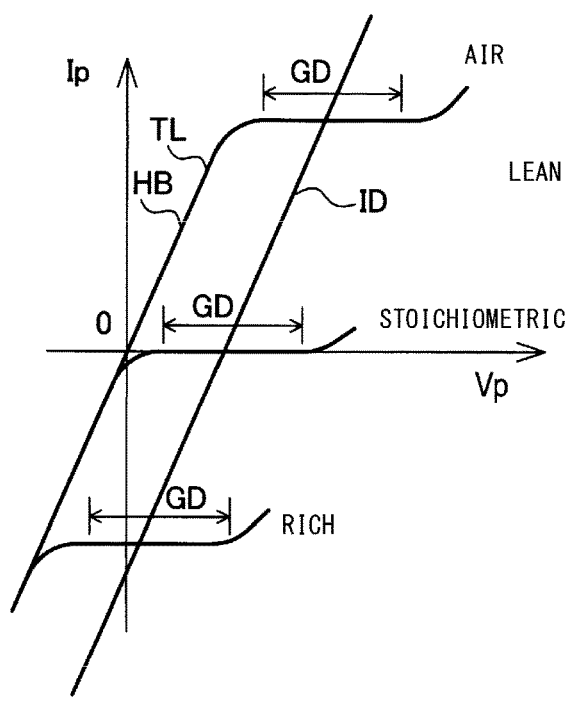
FIG. 4A is a graph which illustrates a basic relationship (V-I characteristics) between voltage and current of the air/fuel ratio sensor, and a limiting current region which changes in accordance with an air/fuel ratio.

As shown in FIG. 4A, a graph (characteristics line TL) indicating the relationship between the application voltage Vp and the pump current Ip has a proportional part HB in which the pump current Ip changes in proportion to an increase in the application voltage Vp, and a flat part parallel to the voltage axis.

Of these parts, the proportional part HB is a resistance-dominant region influenced by a DC internal resistance Ri (hereinafter, also referred to as a resistance R) of the element portion 10 (specifically, the solid electrolyte layer 11) of the sensor element 9. That is, in the resistance dominant region, as the application voltage Vp increases, the pump current Ip increases in proportion thereto. The resistance R changes in accordance with the temperature (element temperature) of the sensor element 9 (specifically, the solid electrolyte layer 11), as described below.

The flat part is a part in which, even if the application voltage Vp changes, the pump current Ip does not substantially change but remains at a constant value (limiting current). The flat part is a limiting current region GD which indicates the pump current Ip corresponding to the oxygen concentration (i.e., air/fuel ratio), and in which change in the limiting current corresponds to a change in the air/fuel ratio.

That is, as the air/fuel ratio approaches the lean side, the limiting current of the pump current Ip increases, and as the air/fuel ratio approaches the rich side, the limiting current decreases. Therefore, the air/fuel ratio can be calculated from the limiting current.

For example, assuming a simple characteristics line TL as shown in FIG. 4A, a single straight application voltage line ID indicating application voltage characteristics may be set so as to pass through limiting current regions GD according to the respective air/fuel ratios, and the air/fuel ratio may be detected using the application voltage line ID. That is, a predetermined voltage in accordance with the application voltage line ID may be applied and the air/fuel ratio may be calculated based on the pump current Ip (indicating the limiting current) obtained at that time.

However, as described above, in the characteristics line TL, the low-voltage side (the left side in FIG. 4A) with respect to the limiting current region GD is a resistance-dominant region influenced by the resistance R of the solid electrolyte layer 11, and has characteristics which change in accordance with the element temperature.

Figure 4B:
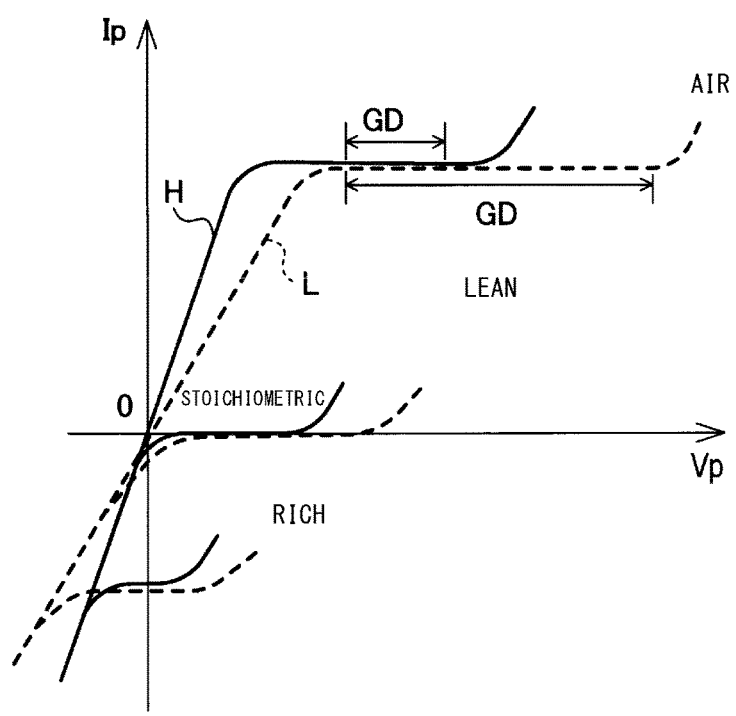
FIG. 4B is a graph which illustrates a basic relationship (V-I characteristics) between voltage and current of the air/fuel ratio sensor, and a resistance-dominant region and a limiting current region which change in accordance with the element temperature.

Specifically, as shown in FIG. 4B, if the element temperature decreases (in case of a low-temperature side L), the resistance R increases and the slope of the straight proportional part HB decreases. On the other hand, if the element temperature increases (in case of a high-temperature side H on which the temperature is higher than on the low-temperature side L), the resistance R decreases and the slope of the straight proportional part HB increases.

In addition, when the element temperature changes as described above, as shown in FIG. 4B, not only the slope (slope of proportional part HB) of the characteristics line TL but also the limiting current region GD changes along the direction of the voltage axis (see, for example, limiting currents GD on high-temperature side H and low-temperature side L in the air).

Therefore, it is necessary to also set the application voltage line ID in consideration of a change in the limiting current region GD due to a change in the element temperature.

Figure 5:
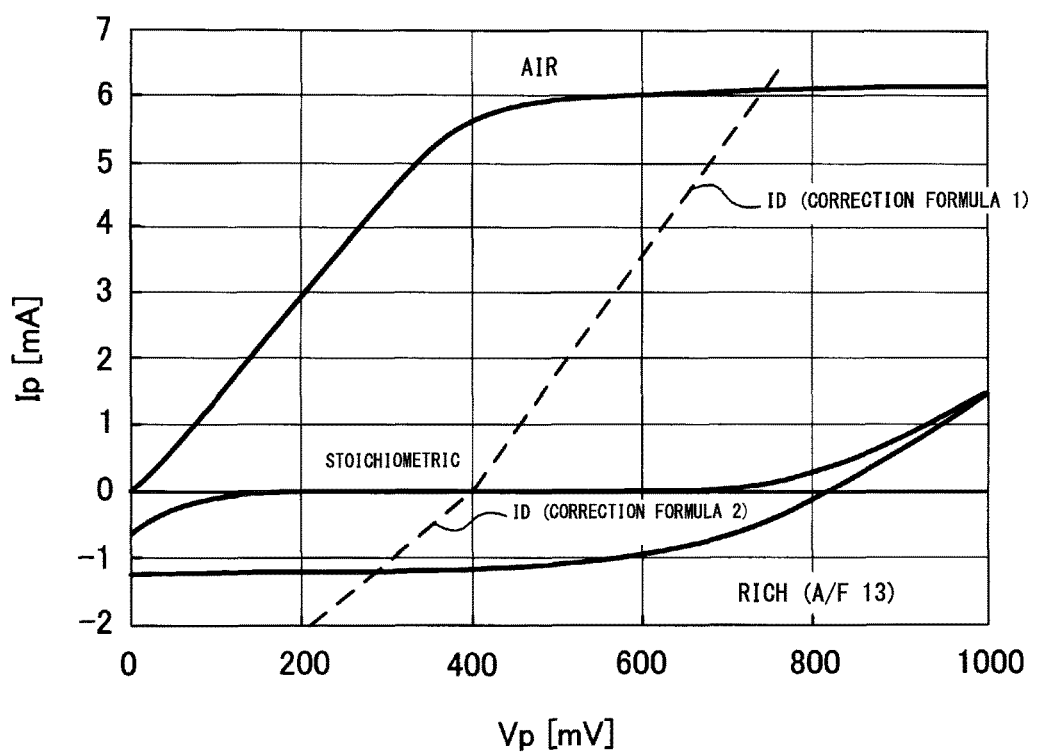
FIG. 5 is a graph which illustrates an application voltage line set by correction formula (1) and correction formula (2) in the first embodiment.

Accordingly, in the present first embodiment, as shown in FIG. 5, a single application voltage line ID is set so as to bend at a stoichiometric point (so that a change in current differs relative to a change in voltage).

More specifically, the application voltage line ID is set by the following correction formulas (1), (2) different between a lean case and a rich case. That is, for a lean case, the application voltage line ID is set as a straight line having a predetermined value (R1) by the following correction formula (1), and for a rich case, the application voltage line ID is set as a straight line having a predetermined value (R2) different from R1 by the following correction formula (2).

The units in the correction formulas (1), (2) are represented as application voltage Vp [mV], pump current Ip [mA], resistance R1 [Ω], resistance R2 [Ω], and voltage value intercept 400 [mV].

$$Vp=Ip \times R1+400 \qquad (1)$$

$$Vp=Ip \times R2+400 \qquad (2)$$

By rearranging correction formulas (1), (2), the following correction formulas (1)', (2)' are obtained, respectively.

$$Ip=Vp \times (1/R1)-(400/R1) \qquad (1)'$$

$$Ip=Vp \times (1/R2)-(400/R2) \qquad (2)'$$

The resistance R1 is an average value of the resistance value of the solid electrolyte layer 11 in a range from a stoichiometric atmosphere to the air atmosphere, and is, for example, 60 [Ω]. The resistance R2 is an average value of the resistance value of the solid electrolyte layer 11 in a range from a stoichiometric atmosphere to a rich atmosphere, and is, for example, 100 [Ω]. The resistance R1 and the resistance R2 have a relationship of R1<R2.

That is, since the application voltage line ID is bent at a stoichiometric point and R1<R2 is satisfied, the slopes of the respective application voltage lines ID shown in a voltage-current coordinate system in FIG. 5 have a relationship of slope (1/R1) of correction formula (1)'>slope (1/R2) of correction formula (2)'.

More specifically, in FIG. 5, the slope (1/R1) of the graph of correction formula (1)' for a lean case is steep, and the slope (1/R2) of the graph of correction formula (2)' for a rich case is smaller than that of correction formula (2) and thus is mild.

The resistance R1 is set such that the application voltage line ID passes through the limiting current regions GD of the characteristics lines TL for a lean case and a stoichiometric case.

On the other hand, the resistance R2 is set such that the application voltage line ID passes through the limiting current regions GD of the characteristics lines TL for a rich case and a stoichiometric case.

Further, in correction formulas (1) and (2), 400 [mV], which is the intercept on the voltage value of the application voltage Vp, is a fixed value at which the characteristics line TL indicates a stoichiometric case and the pump current Ip is 0 [mA]. The reason for setting the value at 400 [mV] is because the characteristics of the sensor element 9 are such that the center of the limiting current region GD in the case where the air/fuel ratio is stoichiometric is 400 [mV].

The correction formulas (1), (2) can be set through an experiment or the like based on the characteristics of the sensor element 9 that are selected.

In FIG. 5, the characteristics lines TL for the case of air and the case where the air/fuel ratio is 13 under a predetermined temperature (for example, 750° C.) are shown. In the present first embodiment, the application voltage lines ID defined by the correction formulas (1), (2) (i.e., the correction formulas (1)', (2)') are set such that, in a predetermined air/fuel ratio detection range (from A/F=10 to air), the application voltage lines ID pass through the limiting current regions GD of the characteristics lines TL in a predetermined temperature range (for example, 630° C. to 1050° C.).

1-4. Control

Next, a process for detecting the oxygen concentration (air/fuel ratio) using the application voltage line ID by the microcomputer 31 will be described.

Figure 6:
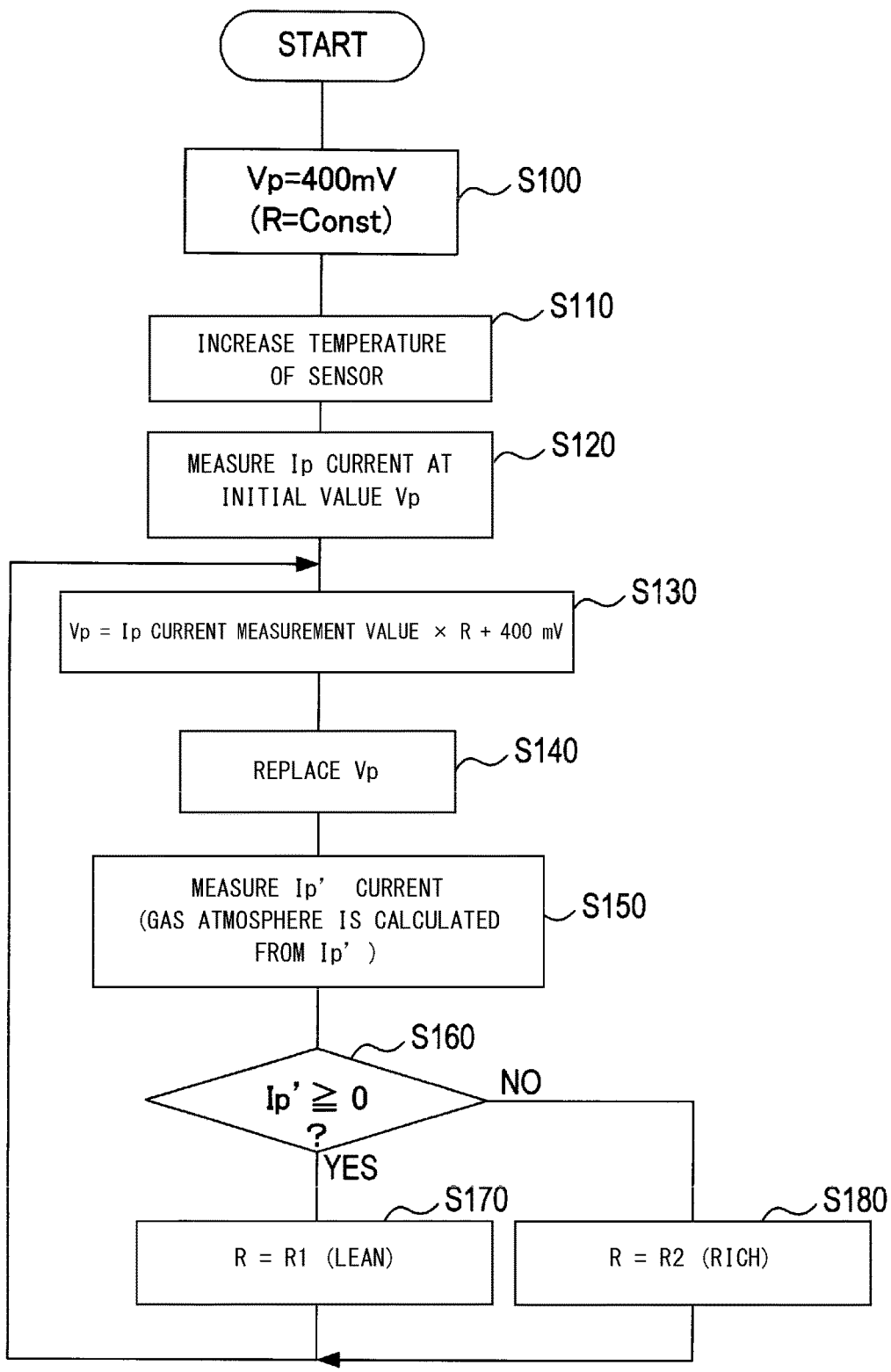
FIG. 6 is a flowchart which illustrates a control process for air/fuel ratio detection in the first embodiment.

As shown in FIG. 6, first, in step (S) 100, 400 [mV] is set as an initial value of the application voltage Vp. At this time, a predetermined fixed value (for example, 60 [Ω]) is set as an initial value R0 of the resistance R.

In the subsequent step 110, control is performed to increase the temperature (element temperature) of the sensor element 9 by applying a voltage to the heater. Thereafter, as is well known to those of ordinary skill in this field of art, the heater is controlled so as to keep the element temperature at a target temperature.

In the subsequent step 120, at the target temperature, a voltage of 400 [mV] set in step 100 is applied between the pair of electrodes 25, 27, using the electric control circuit 33, and the pump current Ip flowing between the pair of electrodes 25, 27 at that time is measured.

In the subsequent step 130, the application voltage Vp is calculated by applying the measurement value (Ip current measurement value) of the pump current Ip measured in step 120 to correction formula (1) (here, an initial value R0 is used as the resistance R), for example.

In the subsequent step 140, the application voltage Vp is replaced. That is, the application voltage Vp calculated in step 130 is used as the voltage to be applied between the pair of electrodes 25, 27.

In the subsequent step 150, the application voltage Vp replaced in the step 140 is applied between the pair of electrodes 25, 27, and pump current I'p flowing between the pair of electrodes 25, 27 by the application is measured.

Since the measured pump current I'p corresponds to the oxygen concentration, the oxygen concentration can be calculated from the pump current I'p. Since the oxygen concentration corresponds to the air/fuel ratio, the air/fuel ratio can be calculated from the pump current I'p, using a map or the like.

In the subsequent step 160, a determination is made as to whether or not the pump current I'p is equal to or greater than 0 [mA]. If the determination result is positive, the process proceeds to step 170. On the other hand, if the determination result is negative, the process proceeds to step 180.

In step 170, since the pump current I'p is equal to or greater than 0 [mA] and thus indicates that the air/fuel ratio is lean, the resistance R1 for lean is set as the resistance R, and the process returns to step 130.

That is, in order to use correction formula (1) shown in FIG. 5 as the application voltage line ID for a lean case, the resistance R1 for lean is set as the resistance R.

On the other hand, in step 180, since the pump current I'p is less than 0 [mA] and thus indicates that the air/fuel ratio is rich, the resistance R2 for rich is set as the resistance R, and the process returns to step 130.

That is, in order to use correction formula (2) shown in FIG. 5 as the application voltage line ID for a rich case, the resistance R2 (here, R1<R2) for rich is set as the resistance R.

1-5. Effects

In the first embodiment, as a basic configuration, the application voltage line ID is set so as to pass through the respective limiting current regions GD for different oxygen concentrations (i.e., air/fuel ratios), and pass through a region in which the respective limiting current regions GD for different temperature conditions of the sensor element 9 (specifically, element portion 10) overlap each other.

In addition, in the first embodiment, in the basic configuration described above, the ratio of change in current with respect to a change in voltage in the application voltage line ID (which is a linear function) is switched in accordance with whether the air/fuel ratio is lean or rich.

Specifically, as the application voltage line ID, correction formula (1) is used in a lean case, and correction formula (2) is used in a rich case. That is, as the resistance R used for correction formulas (1), (2), R1 is used in a lean case, and R2 (here, R1<R2) is used in a rich case.

That is, for correction formulas (1)', (2)', in a lean case, (1/R1) having a greater value is used as a ratio for lean, and in a rich case, (1/R2) having a smaller value is used as a ratio for rich. It is noted that, since R1<R2 is satisfied, 1/R1>1/R2 is satisfied. Thus, it is possible to detect the air/fuel ratio with higher accuracy.

That is, even when considering the temperature condition, for example, depending on the oxygen concentration or the like, the application voltage line ID using a single straight line can deviate from some limiting current regions GD, and in this case, it might be impossible to accurately detect the air/fuel ratio even if control using this application voltage line ID is performed. However, in the first embodiment, a change ratio (i.e., 1/R1, 1/R2) that differs between a lean case and a rich case is set, whereby the application voltage line ID can be prevented from deviating from the limiting current regions GD.

Therefore, by using the application voltage line ID set as described above, it is possible to detect the air/fuel ratio with higher accuracy.

In addition, in the first embodiment, the resistance R1, R2 (i.e., ratio for lean (1/R1), ratio for rich (1/R2)) is switched based on the current flowing between the pair of electrodes 25, 27.

That is, since the pump current Ip flowing between the pair of electrodes 25, 27 corresponds to the air/fuel ratio, the resistance R1, R2 is switched in accordance with the pump current Ip, whereby the application voltage line ID that is unlikely to deviate from the limiting current regions GD can be set.

1-6. Term Correspondence

Here, the relationship between corresponding terms used to define the invention and the first embodiment will be described.

The solid electrolyte layer 11, the electrodes 25, 27, the air/fuel ratio sensor 5, and the gas concentration detection device 7 in the first embodiment respectively correspond to examples of a solid electrolyte, electrodes, a gas concentration sensor, and a gas concentration detection device in the present invention.

2. Second Embodiment

Next, the second embodiment will be described, while description of the same content as in the first embodiment is omitted. The same components as in the first embodiment are indicated by the same reference numerals as in the first embodiment.

The present second embodiment is different from the first embodiment with respect to its control process, and therefore the difference will be described.

Figure 7:
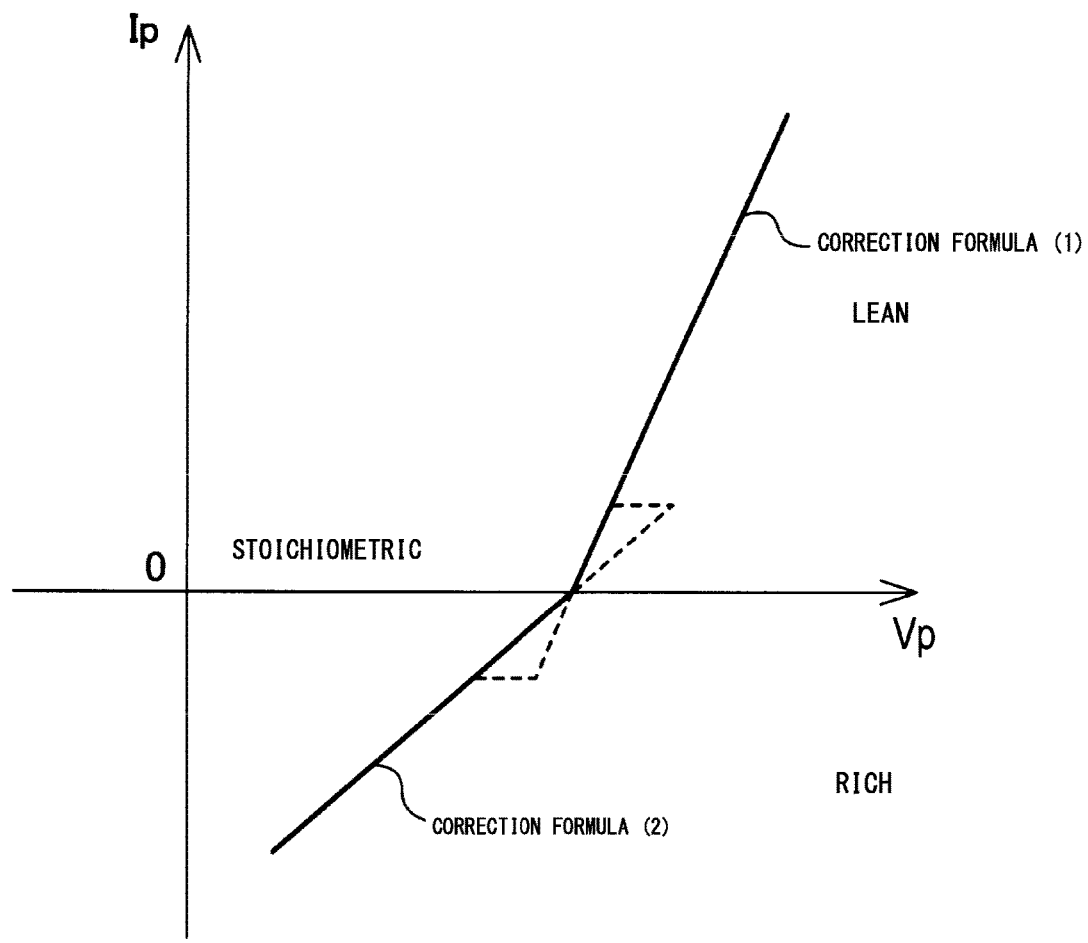
FIG. 7 is a graph which illustrates hysteresis for timing the switching between correction formula (1) and correction formula (2) in a second embodiment.

That is, in the present second embodiment, hysteresis as shown by a broken line in FIG. 7 is set for switching between correction formula (1) and correction formula (2), whereby frequent switching in the vicinity of a stoichiometric state is prevented. Hereinafter, the control process therefor will be described in detail.

Figure 8:
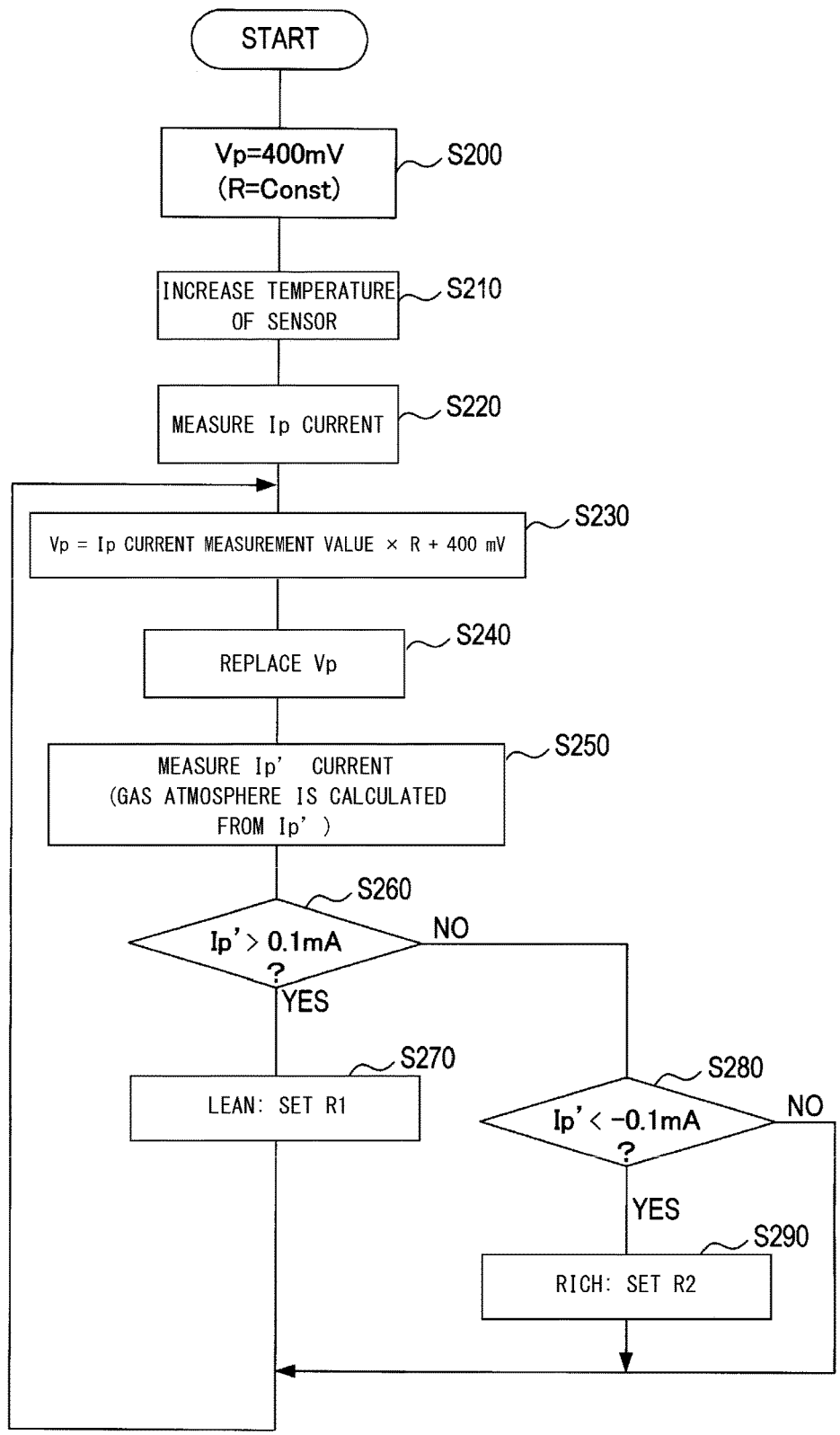
FIG. 8 is a flowchart which illustrates a control process for air/fuel ratio detection in the second embodiment.

As shown in FIG. 8, first, a process from step 200 to step 250 is the same as the process from step 100 to step 150 in the first embodiment.

That is, in step 200, 400 [mV] is set as the application voltage Vp.

In the subsequent step 210, the temperature (element temperature) of the sensor element 9 is controlled.

In the subsequent step 220, a voltage of 400 [mV] is applied between the pair of electrodes 25, 27, and the pump current Ip at that time is measured.

In the subsequent step 230, the application voltage Vp is calculated by applying the Ip current measurement value measured in step 220 to correction formula (1), for example.

In the subsequent step 240, the application voltage Vp is replaced.

In the subsequent step 250, the replaced application voltage Vp is applied between the pair of electrodes 25, 27, and the pump current I'p is measured.

Then, in step 260, a determination is made as to whether or not the pump current I'p measured in step 250 is greater than 0.1 [mA]. If the determination result is positive, the process proceeds to step 270. On the other hand, if the determination result is negative, the process proceeds to step 280.

In step 270, since the pump current I'p is greater than 0.1 [mA], the resistance R1 for lean is set as the resistance R for correction formula (1), and the process proceeds to step 230.

Therefore, in this case, in step 230, the application voltage Vp is calculated using correction formula (1).

On the other hand, in step 280, a determination is made as to whether or not the pump current I'p measured in step 250 is smaller than −0.1 [mA]. If the determination result is positive, the process proceeds to step 290. On the other hand, if the determination result is negative, the process proceeds to step 230.

In step 290, since the pump current I'p is smaller than −0.1 [mA], the resistance R2 for rich is set as the resistance R for correction formula (2), and the process returns to step 230.

Therefore, in this case, in step 230, the application voltage Vp is calculated using correction formula (2).

In the case where the determination result in step 280 is negative and the process returns to step 230, the application voltage Vp is calculated using the previous correction formula (1) or (2) to which the previous resistance (R1 or R2) is applied, without switching the resistance R.

Owing to the configuration described above, in the present second embodiment, the same effect as in the first embodiment is provided. In addition, as described above, instead of immediately switching the resistance R1, R2 at a stoichiometric point to switch the correction formula (1), (2), hysteresis is set to shift a timing of switching the correction formula (1), (2), whereby the correction formula can be prevented from being immediately switched at a stoichiometric point.

In particular, in the case where the target air/fuel ratio is set at a stoichiometric ratio, by setting the hysteresis as described above, frequent switching of the correction formula (1), (2) can be prevented, and therefore there is an advantage that the air/fuel ratio can be stably controlled to be the target air/fuel ratio.

3. Third Embodiment

Next, the third embodiment will be described, while description of the same content as in the second embodiment is omitted. It is noted that the same components as in the second embodiment are indicated by the same reference numerals as in the second embodiment.

The control process of the third embodiment differs from that of the second embodiment, and therefore this difference will be described.

That is, in the present third embodiment, hysteresis is set using a counter, for switching between correction formula (1) and correction formula (2). Hereinafter, the control process therefor will be described in detail.

Figure 9:
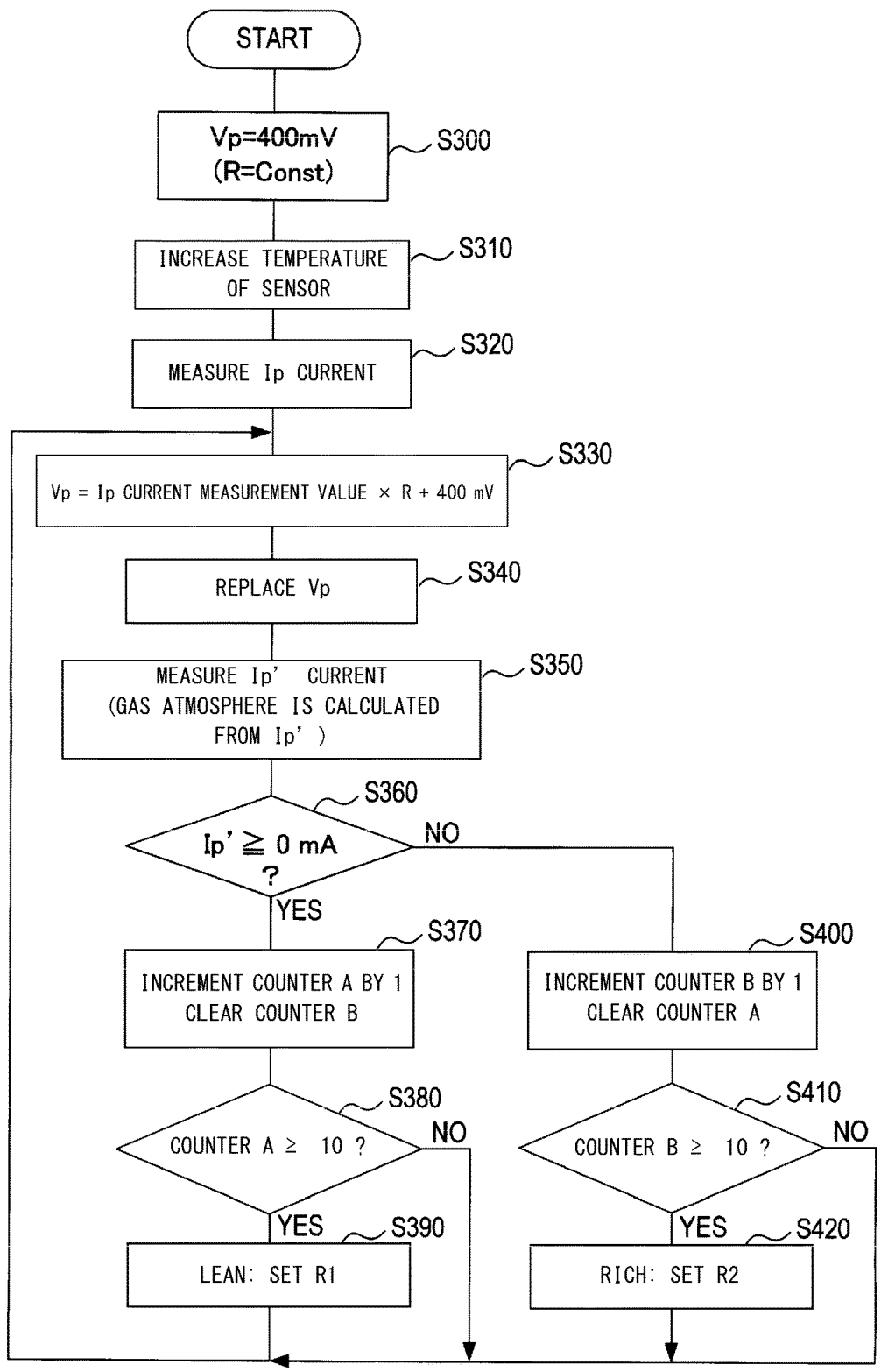
FIG. 9 is a flowchart which illustrates a control process for air/fuel ratio detection in a third embodiment.

As shown in FIG. 9, first, a process from step 300 to step 350 is the same as the process from step 100 to step 150 in the first embodiment.

That is, in step 300, 400 [mV] is set as the application voltage Vp.

In the subsequent step 310, the temperature (element temperature) of the sensor element 9 is controlled.

In the subsequent step 320, a voltage of 400 [mV] is applied between the pair of electrodes 25, 27, and the pump current Ip at that time is measured.

In the subsequent step 330, the application voltage Vp is calculated by substituting the Ip current measurement value measured in step 320 into correction formula (1), for example.

In the subsequent step 340, the application voltage Vp is replaced with the value calculated from the correction formula (1).

In the subsequent step 350, the replaced application voltage Vp is applied between the pair of electrodes 25, 27, and the pump current I'p is measured.

Then, in step 360, a determination is made as to whether or not the pump current I'p measured in step 350 is equal to or greater than 0 [mA]. If the determination result is positive, the process proceeds to step 370. On the other hand, if the determination result is negative, the process proceeds to step 400.

In step 370, a counter A is incremented by 1, and a counter B is cleared.

In the subsequent step 380, a determination is made as to whether or not the counter A is equal to or greater than 10. If the determination result is positive, the process proceeds to step 390, and on the other hand, if the determination result is negative, the process returns to step 330.

In step 390, since a predetermined time corresponding to a value of 10 or more of the counter A has elapsed (from when the pump current I'p becomes equal to or greater than 0 [mA]), the resistance R1 for lean is set as the resistance R for correction formula (1), and the process returns to step 330. In addition, although not shown, in step 390, the counter A is cleared.

Therefore, in this case, in step 330, the application voltage Vp is calculated using correction formula (1).

In the case where the determination result in step 380 is negative, the hysteresis time has not yet elapsed, and therefore the process returns to step 330 to again repeat the same process.

On the other hand, in step 400 subsequent to a negative determination in step 360, the counter B is incremented by 1, and the counter A is cleared.

In the subsequent step 410, a determination is made as to whether or not the counter B is equal to or greater than 10. If the determination result is positive, the process proceeds to step 420. On the other hand, if the determination result is negative, the process returns to step 330.

In step 420, since a predetermined time corresponding to a value of 10 or more of the counter B has elapsed (from when the pump current I'p becomes smaller than 0 [mA]), the resistance R2 for rich is set as the resistance R for correction formula (2), and the process returns to step 330. In addition, although not shown, the counter B is cleared in step 420.

Therefore, in this case, in step 330, the application voltage Vp is calculated using correction formula (2).

In the case where the determination result in step 410 is negative, the hysteresis time has not yet elapsed, and therefore the process returns to step 330 again to repeat the same process.

Owing to the configuration described above, in the present third embodiment, the same effect as in the second embodiment is obtained. That is, as described above, instead of immediately switching the resistance R1, R2 at a stoichiometric point so as to switch the correction formula (1), (2), hysteresis is set to shift a timing of switching the correction formula (1), (2). Consequently, the correction formula is prevented from being immediately switched at a stoichiometric point. Therefore, there is an advantage that, for example, even in the case where the target air/fuel ratio is set to the stoichiometric ratio, the air/fuel ratio can be stably controlled.

4. Other Embodiments

While certain embodiments of the present invention have been described above, the present invention is not limited thereto, but may be modified in various ways without deviating from the gist of the present invention.

(1) For example, although a predetermined fixed value (400 [mV]) is used as the intercept on the application voltage of the correction formula in the above embodiments, another value (e.g., 450 [mV]) may be used.

(2) Although R1 (e.g., 60 [Ω]) and R2 (e.g., 100 [Ω]) are respectively used as the resistances R for the correction formulas (1), (2), other values that satisfy R1<R2 may be used.

(3) In the above embodiments, a gas concentration detection device that detects an oxygen concentration using an oxygen sensor (air/fuel ratio sensor) for detecting the oxygen concentration has been shown. However, the present invention is also applicable to a gas concentration detection device that detects a gas concentration of NOx, H2O, or the like, for example.

(4) The components in the above embodiments may be combined as appropriate.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2016-100623 filed May 19, 2016, incorporated herein by reference in its entirety.

What is claimed is:

1. A gas concentration detection device, adapted for a gas concentration sensor including a sensor element having: a solid electrolyte having oxygen ion conductivity; and a pair of electrodes formed on the solid electrolyte, the gas concentration detection device being configured to apply a voltage between the pair of electrodes based on an application voltage line which is a linear function having an intercept at a predetermined voltage value, detect a limiting current flowing between the pair of electrodes in accordance with the voltage, and detect a gas concentration of a specific component in a gas to be measured, based on the limiting current, wherein
   in a detection range for detecting the gas concentration, the application voltage line is set so as to pass through a plurality of limiting current regions of respective limiting current regions for different values of the gas concentration; and a region in which respective limiting current regions for different temperature conditions of the sensor element overlap each other, and
   a ratio of change in current with respect to a change in voltage in the application voltage line is set as a ratio for lean when an air/fuel ratio corresponding to the gas concentration is lean, and a ratio for rich different from the ratio for lean is set when the air/fuel ratio is rich.

2. The gas concentration detection device as claimed in claim 1, wherein
   the ratio for lean is greater than the ratio for rich.

3. The gas concentration detection device as claimed in claim 1,
   which is configured to switch between the ratio for rich and the ratio for lean based on the limiting current flowing between the pair of electrodes.

4. The gas concentration detection device as claimed in claim 1, wherein
   when the air/fuel ratio is lean and the ratio for lean is set, the gas concentration device is configured so that the ratio for lean remains set within a rich-side hysteresis range set in a predetermined rich-side range from a stoichiometric state when the air/fuel ratio changes from lean to rich.

5. The gas concentration detection device as claimed in claim 1, wherein
   when the air/fuel ratio is rich and the ratio for rich is set, the gas concentration device is configured so that the ratio for rich remains set within a lean-side hysteresis range set in a predetermined lean-side range from a stoichiometric state when the air/fuel ratio changes from rich to lean.

* * * * *